(12) United States Patent
Dishler et al.

(10) Patent No.: US 8,469,948 B2
(45) Date of Patent: Jun. 25, 2013

(54) METHODS AND DEVICES FOR FORMING CORNEAL CHANNELS

(75) Inventors: Jon Dishler, Cherry Hills Village, CO (US); Ned Schneider, Aliso Viejo, CA (US)

(73) Assignee: ReVision Optics, Inc., Lake Forest, CA (US)

( * ) Notice: Subject to any disclaimer, the term of this patent is extended or adjusted under 35 U.S.C. 154(b) by 84 days.

(21) Appl. No.: 12/861,656

(22) Filed: Aug. 23, 2010

(65) Prior Publication Data

US 2012/0046680 A1 Feb. 23, 2012

(51) Int. Cl.
*A61B 18/18* (2006.01)

(52) U.S. Cl.
USPC .............................................................. 606/5

(58) Field of Classification Search
USPC ................. 606/4–6, 107, 166; 623/5.11–5.16
See application file for complete search history.

(56) References Cited

U.S. PATENT DOCUMENTS

| | | |
|---|---|---|
| 2,714,721 A | 8/1955 | Stone, Jr. |
| 3,091,328 A | 5/1963 | Leonardos |
| 3,168,100 A | 2/1965 | Rich |
| 3,343,657 A | 9/1967 | Speshyock |
| 3,379,200 A | 4/1968 | Pennell |
| 3,482,906 A | 12/1969 | Volk |
| 3,743,337 A | 7/1973 | Crary |
| 3,770,113 A | 11/1973 | Thomas |
| 3,879,076 A | 4/1975 | Barnett |
| 3,950,315 A | 4/1976 | Cleaver |
| 3,996,627 A | 12/1976 | Deeg et al. |
| 4,030,480 A | 6/1977 | Meyer |
| 4,037,604 A | 7/1977 | Newkirk |
| 4,039,827 A | 8/1977 | Zdrok et al. |
| 4,065,816 A | 1/1978 | Sawyer |
| 4,071,272 A | 1/1978 | Drdlik |
| 4,093,291 A | 6/1978 | Schurgin |
| 4,136,406 A | 1/1979 | Norris |
| 4,157,718 A | 6/1979 | Baehr |
| 4,184,491 A | 1/1980 | McGannon |
| 4,194,814 A | 3/1980 | Fischer et al. |
| 4,238,524 A | 12/1980 | LaLiberte et al. |
| 4,257,521 A | 3/1981 | Poler |
| 4,268,133 A | 5/1981 | Fischer et al. |
| 4,326,306 A | 4/1982 | Poler |
| 4,357,940 A | 11/1982 | Muller |
| 4,392,569 A | 7/1983 | Shoup |
| 4,418,991 A | 12/1983 | Breger |
| 4,423,809 A | 1/1984 | Mazzocco |

(Continued)

FOREIGN PATENT DOCUMENTS

| | | |
|---|---|---|
| DE | 3208729 A1 | 9/1983 |
| EP | 0308077 A2 | 3/1989 |

(Continued)

OTHER PUBLICATIONS

Alio, J. J., et al., "Intracorneal Inlay Complicated by Intrastomal Epithelial Opacification," Arch Ophthalmol, vol. 122, Oct. 2004.

(Continued)

*Primary Examiner* — Ryan Severson
*Assistant Examiner* — David Eastwood
(74) *Attorney, Agent, or Firm* — Shay Glenn LLP

(57) ABSTRACT

Instruments for creating a corneal channel and methods of use.

23 Claims, 17 Drawing Sheets

U.S. PATENT DOCUMENTS

| | | |
|---|---|---|
| 4,428,746 A | 1/1984 | Mendez |
| 4,452,235 A | 6/1984 | Reynolds |
| 4,466,705 A | 8/1984 | Michelson |
| 4,490,860 A | 1/1985 | Rainin |
| 4,504,982 A | 3/1985 | Burk |
| 4,521,210 A | 6/1985 | Wong |
| 4,525,044 A | 6/1985 | Bauman |
| 4,545,478 A | 10/1985 | Waldman |
| 4,554,115 A | 11/1985 | Neefe |
| 4,554,918 A | 11/1985 | White |
| 4,565,198 A | 1/1986 | Koeniger |
| 4,580,882 A | 4/1986 | Nuchman et al. |
| 4,586,929 A | 5/1986 | Binder |
| 4,604,087 A | 8/1986 | Joseph |
| 4,607,617 A | 8/1986 | Choyce |
| 4,616,910 A | 10/1986 | Klein |
| 4,618,227 A | 10/1986 | Bayshore |
| 4,619,256 A | 10/1986 | Horn |
| 4,624,664 A | 11/1986 | Peluso et al. |
| 4,624,669 A | 11/1986 | Grendahl |
| 4,640,595 A | 2/1987 | Volk |
| 4,646,720 A | 3/1987 | Peyman et al. |
| 4,655,774 A | 4/1987 | Choyce |
| 4,662,370 A | 5/1987 | Hoffmann et al. |
| 4,663,358 A | 5/1987 | Hyon et al. |
| 4,671,276 A | 6/1987 | Reynolds |
| 4,676,792 A | 6/1987 | Praeger |
| 4,697,697 A | 10/1987 | Graham et al. |
| 4,702,244 A | 10/1987 | Mazzocco |
| 4,709,697 A | 12/1987 | Muller |
| 4,721,124 A | 1/1988 | Tuerkheimer et al. |
| 4,726,367 A | 2/1988 | Shoemaker |
| 4,750,901 A | 6/1988 | Molteno |
| 4,762,496 A | 8/1988 | Maloney et al. |
| 4,766,895 A | 8/1988 | Reynolds |
| 4,769,033 A | 9/1988 | Nordan |
| 4,772,283 A | 9/1988 | White |
| 4,778,462 A | 10/1988 | Grendahl |
| 4,798,609 A | 1/1989 | Grendahl |
| 4,806,382 A | 2/1989 | Goldberg et al. |
| 4,836,201 A | 6/1989 | Patton et al. |
| 4,840,175 A | 6/1989 | Peyman |
| 4,842,599 A | 6/1989 | Bronstein |
| 4,844,242 A | 7/1989 | Chen et al. |
| 4,851,003 A | 7/1989 | Lindstrom |
| 4,860,885 A | 8/1989 | Kaufman et al. |
| 4,886,488 A | 12/1989 | White |
| 4,888,016 A | 12/1989 | Langerman |
| 4,897,981 A | 2/1990 | Beck |
| 4,911,715 A | 3/1990 | Kelman |
| 4,919,130 A | 4/1990 | Stoy et al. |
| 4,923,467 A | 5/1990 | Thompson |
| 4,934,363 A | 6/1990 | Smith et al. |
| 4,936,825 A | 6/1990 | Ungerleider |
| 4,946,436 A | 8/1990 | Smith |
| 4,955,903 A | 9/1990 | Sulc et al. |
| 4,968,296 A | 11/1990 | Ritch et al. |
| 4,971,732 A | 11/1990 | Wichterle |
| 4,976,719 A | 12/1990 | Siepser |
| 5,019,084 A | 5/1991 | Aysta et al. |
| 5,019,098 A | 5/1991 | Mercier |
| 5,022,414 A | 6/1991 | Muller |
| 5,030,230 A | 7/1991 | White |
| 5,041,081 A | 8/1991 | Odrich |
| 5,063,942 A | 11/1991 | Kilmer et al. |
| 5,071,276 A | 12/1991 | Nielsen et al. |
| 5,073,163 A | 12/1991 | Lippman |
| 5,092,837 A | 3/1992 | Ritch et al. |
| 5,098,444 A | 3/1992 | Feaster |
| 5,108,428 A | 4/1992 | Capecchi et al. |
| 5,112,350 A | 5/1992 | Civerchia et al. |
| 5,123,905 A | 6/1992 | Kelman |
| 5,123,921 A | 6/1992 | Werblin et al. |
| 5,139,518 A | 8/1992 | White |
| 5,171,213 A | 12/1992 | Price, Jr. |
| 5,173,723 A | 12/1992 | Volk |
| 5,178,604 A | 1/1993 | Baerveldt et al. |
| 5,180,362 A | 1/1993 | Worst et al. |
| 5,181,053 A | 1/1993 | Brown |
| 5,188,125 A | 2/1993 | Kilmer et al. |
| 5,190,552 A | 3/1993 | Kelman |
| 5,192,317 A | 3/1993 | Kalb |
| 5,196,026 A | 3/1993 | Barrett et al. |
| 5,211,660 A | 5/1993 | Grasso |
| 5,225,858 A | 7/1993 | Portney |
| 5,229,797 A | 7/1993 | Futhey et al. |
| 5,244,799 A | 9/1993 | Anderson |
| 5,258,042 A | 11/1993 | Mehta |
| 5,270,744 A | 12/1993 | Portney |
| 5,273,750 A | 12/1993 | Homiger et al. |
| 5,282,851 A | 2/1994 | Jacob-LaBarre |
| 5,300,020 A | 4/1994 | L'Esperance, Jr. |
| 5,300,116 A | 4/1994 | Chirila et al. |
| 5,312,413 A | 5/1994 | Eaton et al. |
| 5,318,044 A | 6/1994 | Kilmer et al. |
| 5,318,046 A | 6/1994 | Rozakis |
| 5,318,047 A | 6/1994 | Davenport et al. |
| 5,336,261 A | 8/1994 | Barrett et al. |
| 5,338,291 A | 8/1994 | Speckman et al. |
| 5,344,448 A | 9/1994 | Schneider et al. |
| 5,346,464 A | 9/1994 | Camras |
| 5,370,607 A | 12/1994 | Memmen |
| 5,372,577 A | 12/1994 | Ungerleider |
| 5,385,582 A | 1/1995 | Ommaya |
| 5,391,201 A | 2/1995 | Barrett et al. |
| 5,397,300 A | 3/1995 | Baerveldt et al. |
| 5,405,384 A | 4/1995 | Silvestrini |
| 5,428,412 A | 6/1995 | Stoyan |
| 5,433,701 A | 7/1995 | Rubinstein |
| 5,454,796 A | 10/1995 | Krupin |
| 5,458,819 A | 10/1995 | Chirila et al. |
| 5,467,149 A | 11/1995 | Morrison et al. |
| 5,474,562 A | 12/1995 | Orchowski et al. |
| 5,476,445 A | 12/1995 | Baerveldt et al. |
| 5,489,301 A | 2/1996 | Barber |
| 5,493,350 A | 2/1996 | Seidner |
| 5,502,518 A | 3/1996 | Lieberman |
| 5,512,220 A | 4/1996 | Roffman et al. |
| 5,520,631 A | 5/1996 | Nordquist et al. |
| 5,521,656 A | 5/1996 | Portney |
| 5,530,491 A | 6/1996 | Baude et al. |
| 5,533,997 A | 7/1996 | Ruiz |
| 5,570,142 A | 10/1996 | Lieberman |
| 5,591,185 A | 1/1997 | Kilmer et al. |
| 5,598,234 A | 1/1997 | Blum et al. |
| 5,616,148 A | 4/1997 | Eagles et al. |
| 5,620,450 A | 4/1997 | Eagles et al. |
| 5,628,794 A | 5/1997 | Lindstrom |
| 5,630,810 A | 5/1997 | Machat |
| 5,634,943 A | 6/1997 | Villain et al. |
| 5,643,276 A | 7/1997 | Zaleski |
| 5,657,108 A | 8/1997 | Portney |
| 5,682,223 A | 10/1997 | Menezes et al. |
| 5,684,560 A | 11/1997 | Roffman et al. |
| 5,715,031 A | 2/1998 | Roffman et al. |
| 5,716,633 A | 2/1998 | Civerchia |
| 5,722,948 A | 3/1998 | Gross |
| 5,722,971 A | 3/1998 | Peyman |
| 5,728,155 A | 3/1998 | Anello et al. |
| 5,752,928 A | 5/1998 | de Roulhac et al. |
| 5,755,785 A | 5/1998 | Rowsey et al. |
| 5,766,181 A | 6/1998 | Chambers et al. |
| 5,772,667 A | 6/1998 | Blake |
| 5,779,711 A | 7/1998 | Kritzinger et al. |
| 5,785,674 A | 7/1998 | Mateen |
| 5,800,442 A | 9/1998 | Wolf et al. |
| 5,800,529 A | 9/1998 | Brauker et al. |
| 5,805,260 A | 9/1998 | Roffman et al. |
| 5,810,833 A | 9/1998 | Brady et al. |
| 5,817,115 A | 10/1998 | Nigam |
| 5,824,086 A | 10/1998 | Silvestrini |
| 5,847,802 A | 12/1998 | Menezes et al. |
| 5,855,604 A | 1/1999 | Lee |
| 5,860,984 A | 1/1999 | Chambers et al. |
| 5,872,613 A | 2/1999 | Blum et al. |
| 5,873,889 A | 2/1999 | Chin |
| 5,876,439 A | 3/1999 | Lee |

| | | | | | | |
|---|---|---|---|---|---|---|
| 5,888,243 | A | 3/1999 | Silverstrini | 6,447,520 | B1 | 9/2002 | Ott et al. |
| 5,913,898 | A | 6/1999 | Feingold | 6,458,141 | B1 | 10/2002 | Peyman |
| 5,919,185 | A | 7/1999 | Peyman | 6,461,384 | B1 | 10/2002 | Hoffmann et al. |
| 5,928,245 | A | 7/1999 | Wolf et al. | 6,471,708 | B2 | 10/2002 | Green |
| 5,929,968 | A | 7/1999 | Cotie et al. | 6,474,814 | B1 | 11/2002 | Griffin |
| 5,929,969 | A | 7/1999 | Roffman | 6,506,200 | B1 | 1/2003 | Chin |
| 5,941,583 | A | 8/1999 | Raimondi | 6,511,178 | B1 | 1/2003 | Roffman et al. |
| 5,944,752 | A | 8/1999 | Silvestrini | 6,527,389 | B2 | 3/2003 | Portney |
| 5,945,498 | A | 8/1999 | Hopken et al. | 6,537,283 | B2 | 3/2003 | Van Noy |
| 5,964,748 | A | 10/1999 | Peyman | 6,543,610 | B1 | 4/2003 | Nigam |
| 5,964,776 | A | 10/1999 | Peyman | 6,544,286 | B1 | 4/2003 | Perez |
| 5,968,065 | A | 10/1999 | Chin | 6,551,307 | B2 * | 4/2003 | Peyman .................... 606/5 |
| 5,976,150 | A | 11/1999 | Copeland | 6,554,424 | B1 | 4/2003 | Miller et al. |
| 5,976,168 | A | 11/1999 | Chin | 6,554,425 | B1 | 4/2003 | Roffman et al. |
| 5,980,549 | A | 11/1999 | Chin | 6,557,998 | B2 | 5/2003 | Portney |
| 6,007,510 | A | 12/1999 | Nigam | 6,581,993 | B2 | 6/2003 | Nigam |
| 6,010,510 | A | 1/2000 | Brown et al. | 6,582,076 | B1 | 6/2003 | Roffman et al. |
| 6,024,448 | A | 2/2000 | Wu et al. | 6,589,203 | B1 | 7/2003 | Mitrev |
| 6,033,395 | A | 3/2000 | Peyman | 6,589,280 | B1 | 7/2003 | Koziol |
| 6,036,714 | A | 3/2000 | Chin | 6,592,591 | B2 | 7/2003 | Polla et al. |
| 6,050,999 | A | 4/2000 | Paraschac et al. | 6,596,000 | B2 | 7/2003 | Chan et al. |
| 6,055,990 | A | 5/2000 | Thompson | 6,605,093 | B1 | 8/2003 | Blake |
| 6,066,170 | A | 5/2000 | Lee | 6,607,537 | B1 | 8/2003 | Binder |
| 6,068,642 | A | 5/2000 | Johnson et al. | 6,607,556 | B1 | 8/2003 | Nigam |
| 6,079,826 | A | 6/2000 | Appleton et al. | 6,623,522 | B2 | 9/2003 | Nigam |
| 6,083,231 | A | 7/2000 | Van Noy et al. | 6,626,941 | B2 | 9/2003 | Nigam |
| 6,086,202 | A | 7/2000 | Chateau et al. | 6,629,979 | B1 | 10/2003 | Feingold et al. |
| 6,090,141 | A | 7/2000 | Lindstrom | 6,632,244 | B1 | 10/2003 | Nigam |
| 6,102,946 | A | 8/2000 | Nigam | 6,645,246 | B1 | 11/2003 | Weinschenk, III et al. |
| 6,110,166 | A | 8/2000 | Juhasz et al. | 6,648,877 | B1 | 11/2003 | Juhasz et al. |
| 6,120,148 | A | 9/2000 | Fiala et al. | 6,657,029 | B2 | 12/2003 | Vanderbilt |
| 6,125,294 | A | 9/2000 | Scholl et al. | 6,666,887 | B1 | 12/2003 | Callahan et al. |
| 6,129,733 | A | 10/2000 | Brady et al. | 6,673,112 | B2 | 1/2004 | Nigam |
| 6,139,560 | A | 10/2000 | Kremer | 6,709,103 | B1 | 3/2004 | Roffman et al. |
| 6,142,969 | A | 11/2000 | Nigam | 6,712,848 | B1 | 3/2004 | Wolf et al. |
| 6,143,001 | A | 11/2000 | Brown et al. | 6,723,104 | B2 | 4/2004 | Ott |
| 6,159,241 | A | 12/2000 | Lee et al. | 6,733,507 | B2 | 5/2004 | McNicholas et al. |
| 6,171,324 | B1 | 1/2001 | Cote et al. | 6,733,526 | B2 | 5/2004 | Paul et al. |
| 6,175,754 | B1 | 1/2001 | Scholl et al. | 6,808,262 | B2 | 10/2004 | Chapoy et al. |
| RE37,071 | E | 2/2001 | Gabrielian et al. | 6,824,178 | B2 | 11/2004 | Nigam |
| 6,183,513 | B1 | 2/2001 | Guenthner et al. | 6,849,090 | B2 | 2/2005 | Nigam |
| 6,197,019 | B1 | 3/2001 | Peyman | 6,855,163 | B2 | 2/2005 | Peyman |
| 6,197,057 | B1 | 3/2001 | Peyman et al. | 6,875,232 | B2 | 4/2005 | Nigam |
| 6,197,058 | B1 | 3/2001 | Portney | 6,879,402 | B2 | 4/2005 | Küchel |
| 6,203,538 | B1 | 3/2001 | Peyman | 6,881,197 | B1 | 4/2005 | Nigam |
| 6,203,549 | B1 | 3/2001 | Waldock | 6,893,461 | B2 | 5/2005 | Nigam |
| 6,203,557 | B1 | 3/2001 | Chin | 6,949,093 | B1 | 9/2005 | Peyman |
| 6,206,919 | B1 | 3/2001 | Lee | 6,955,432 | B2 | 10/2005 | Graham |
| 6,210,005 | B1 | 4/2001 | Portney | 7,128,351 | B2 | 10/2006 | Nigam |
| 6,214,015 | B1 | 4/2001 | Reich et al. | 7,776,086 | B2 | 8/2010 | Miller |
| 6,214,044 | B1 | 4/2001 | Silverstrini | 2001/0027314 | A1 * | 10/2001 | Peyman .................... 606/5 |
| 6,217,571 | B1 | 4/2001 | Peyman | 2001/0051826 | A1 | 12/2001 | Bogaert et al. |
| 6,221,067 | B1 | 4/2001 | Peyman | 2002/0010510 | A1 * | 1/2002 | Silvestrini ............. 623/5.12 |
| 6,228,114 | B1 | 5/2001 | Lee | 2002/0055753 | A1 * | 5/2002 | Silvestrini ............. 606/166 |
| 6,248,111 | B1 | 6/2001 | Glick et al. | 2002/0101563 | A1 | 8/2002 | Miyamura et al. |
| 6,250,757 | B1 | 6/2001 | Roffman et al. | 2002/0103538 | A1 | 8/2002 | Hughes et al. |
| 6,251,114 | B1 | 6/2001 | Farmer et al. | 2002/0138069 | A1 * | 9/2002 | Peyman .................... 606/5 |
| 6,264,648 | B1 | 7/2001 | Peyman | 2003/0014042 | A1 * | 1/2003 | Juhasz et al. ............ 606/5 |
| 6,264,670 | B1 | 7/2001 | Chin | 2003/0033010 | A1 | 2/2003 | Hicks et al. |
| 6,264,692 | B1 | 7/2001 | Woffinden et al. | 2003/0069637 | A1 | 4/2003 | Lynch et al. |
| 6,267,768 | B1 | 7/2001 | Deacon et al. | 2003/0078487 | A1 | 4/2003 | Jeffries et al. |
| 6,271,281 | B1 | 8/2001 | Liao et al. | 2003/0229303 | A1 | 12/2003 | Haffner et al. |
| 6,277,137 | B1 | 8/2001 | Chin | 2004/0019379 | A1 | 1/2004 | Glick et al. |
| 6,280,449 | B1 | 8/2001 | Blake | 2004/0034413 | A1 | 2/2004 | Christensen |
| 6,280,470 | B1 | 8/2001 | Peyman | 2004/0054408 | A1 | 3/2004 | Glick et al. |
| 6,283,595 | B1 | 9/2001 | Breger | 2004/0073303 | A1 | 4/2004 | Schanzlin |
| 6,302,877 | B1 | 10/2001 | Ruiz | 2005/0080484 | A1 | 4/2005 | Marmo et al. |
| 6,325,509 | B1 | 12/2001 | Hodur et al. | 2005/0080485 | A1 | 4/2005 | Nigam |
| 6,325,792 | B1 | 12/2001 | Swinger et al. | 2005/0113844 | A1 | 5/2005 | Nigam |
| 6,361,560 | B1 | 3/2002 | Nigam | 2005/0119738 | A1 | 6/2005 | Nigam |
| 6,364,483 | B1 | 4/2002 | Grossinger et al. | 2005/0143717 | A1 | 6/2005 | Peyman |
| 6,371,960 | B2 | 4/2002 | Heyman et al. | 2005/0178394 | A1 | 8/2005 | Slade |
| 6,391,230 | B1 | 5/2002 | Sarbadhikari | 2005/0182350 | A1 | 8/2005 | Nigam |
| 6,398,277 | B1 | 6/2002 | McDonald | 2005/0203494 | A1 | 9/2005 | Holliday |
| 6,398,789 | B1 | 6/2002 | Capetan | 2005/0246016 | A1 | 11/2005 | Miller et al. |
| 6,428,572 | B2 | 8/2002 | Nagai | 2006/0020267 | A1 | 1/2006 | Marmo |
| 6,435,681 | B2 | 8/2002 | Portney | 2006/0116762 | A1 | 6/2006 | Hong et al. |
| 6,436,092 | B1 | 8/2002 | Peyman | 2006/0142780 | A1 | 6/2006 | Pynson et al. |
| 6,447,519 | B1 | 9/2002 | Brady et al. | 2006/0142781 | A1 | 6/2006 | Pynson et al. |

| | | | |
|---|---|---|---|
| 2006/0173539 A1* | 8/2006 | Shiuey | 623/5.11 |
| 2006/0212041 A1 | 9/2006 | Nigam | |
| 2006/0235430 A1 | 10/2006 | Le et al. | |
| 2007/0027538 A1 | 2/2007 | Aharoni et al. | |
| 2007/0106318 A1* | 5/2007 | McDonald | 606/190 |
| 2007/0106376 A1* | 5/2007 | Roberts et al. | 623/4.1 |
| 2007/0129797 A1 | 6/2007 | Lang et al. | |
| 2007/0203577 A1 | 8/2007 | Dishler et al. | |
| 2007/0255401 A1 | 11/2007 | Lang | |
| 2007/0280994 A1 | 12/2007 | Cunanan | |
| 2008/0243138 A1* | 10/2008 | Dishler et al. | 606/107 |
| 2008/0262610 A1 | 10/2008 | Lang et al. | |
| 2009/0198325 A1 | 8/2009 | Holliday et al. | |
| 2009/0216217 A1 | 8/2009 | Odrich et al. | |
| 2011/0290681 A1 | 12/2011 | Nigam | |
| 2012/0165823 A1 | 6/2012 | Dishler et al. | |

FOREIGN PATENT DOCUMENTS

| | | |
|---|---|---|
| EP | 0420549 A2 | 4/1991 |
| JP | 01-195853 | 8/1989 |
| JP | 02-211119 | 8/1990 |
| JP | 5502811 | 5/1993 |
| JP | H06510687 | 12/1994 |
| JP | 08-501009 | 2/1996 |
| JP | 9-504706 | 5/1997 |
| JP | 2000506056 | 5/2000 |
| JP | 2002537895 | 11/2002 |
| JP | 03-508135 | 3/2003 |
| JP | 2007500070 | 1/2007 |
| WO | WO 96/26890 A1 | 9/1996 |
| WO | WO 98/08549 A1 | 3/1998 |
| WO | WO 98/48715 A1 | 11/1998 |
| WO | WO 99/17691 A1 | 4/1999 |
| WO | WO 99/21513 A1 | 5/1999 |
| WO | WO 99/30645 A2 | 6/1999 |
| WO | WO 00/38594 A1 | 7/2000 |
| WO | WO 03/041616 A1 | 5/2003 |
| WO | WO 03/061518 A2 | 7/2003 |
| WO | WO 03/101341 A2 | 12/2003 |
| WO | WO 2005/020792 A2 | 3/2005 |
| WO | WO 2006/029316 A1 | 4/2006 |
| WO | WO 2006/060363 A2 | 6/2006 |
| WO | WO 2007/101016 A2 | 9/2007 |
| WO | WO 2007/132332 A2 | 11/2007 |

OTHER PUBLICATIONS

Cheng, et al.; "Predicting subjective judgment of best focus with objective image quality metrics"; Journal of Vision; vol. 4, pp. 310-321, 2004.

Churms, P.W., "The Theory and Computation of Optical Modifications to the Cornea in Refractive Keratoplasty," American Journal of Optometry & Physiological Optics, 56:2, pp. 67-74, Feb. 1979.

Huang et al.; Mathematical Model of Corneal Surface Smoothing After Laser Refractive Surgery; American Journal of Ophthalmology; Mar. 2003; pp. 267-278.

Lang, A.J. et al., "First order design of intracorneal inlays: dependence on keratometric flap and corneal properties," ARVO Abstracts 2006, poster No. 3591, May 3, 2006.

Liou, H. L. et al., "Anatomically accurate, finite model eye for optical modeling", Journal of the Optical Society of America, vol. 14, No. 8, Aug. 1997.

Marsack, et al.; "Metrics of optical quality derived from wave aberrations predict visual performance"; Journal of Vision; vol. 4; pp. 322-328; 2004.

Navarro et al.; Accommodation-dependent model of the human eye with asphericss; J. Opt. Soc Am. A; vol. 2; No. 8; Aug. 1985; pp. 1273-1281.

Watsky, M.A. et al., "Predicting Refractive Alterations with Hydrogel Keratophakia," Investigative Opthalmology & Visual Science, vol. 26, pp. 240-243, Feb. 1985.

Dishler et al.; U.S. Appl. No. 12/877,799 entitled "Small Diameter Inlays," filed Sep. 8, 2010.

Schneider et al.; U.S. Appl. No. 13/549,007 entitled "Corneal Implant Retaining Devices and Methods of Use," filed Jul. 13, 2012.

Schneider et al.; U.S. Appl. No. 13/619,955 entitled "Corneal Implant Inserters and Methods of Use," filed Sep. 14, 2012.

Nigam, Alok; U.S. Appl. No. 13/443,696 entitled "System for Packaging and Handling an Implant and Method of Use," filed Apr. 10, 2012.

* cited by examiner

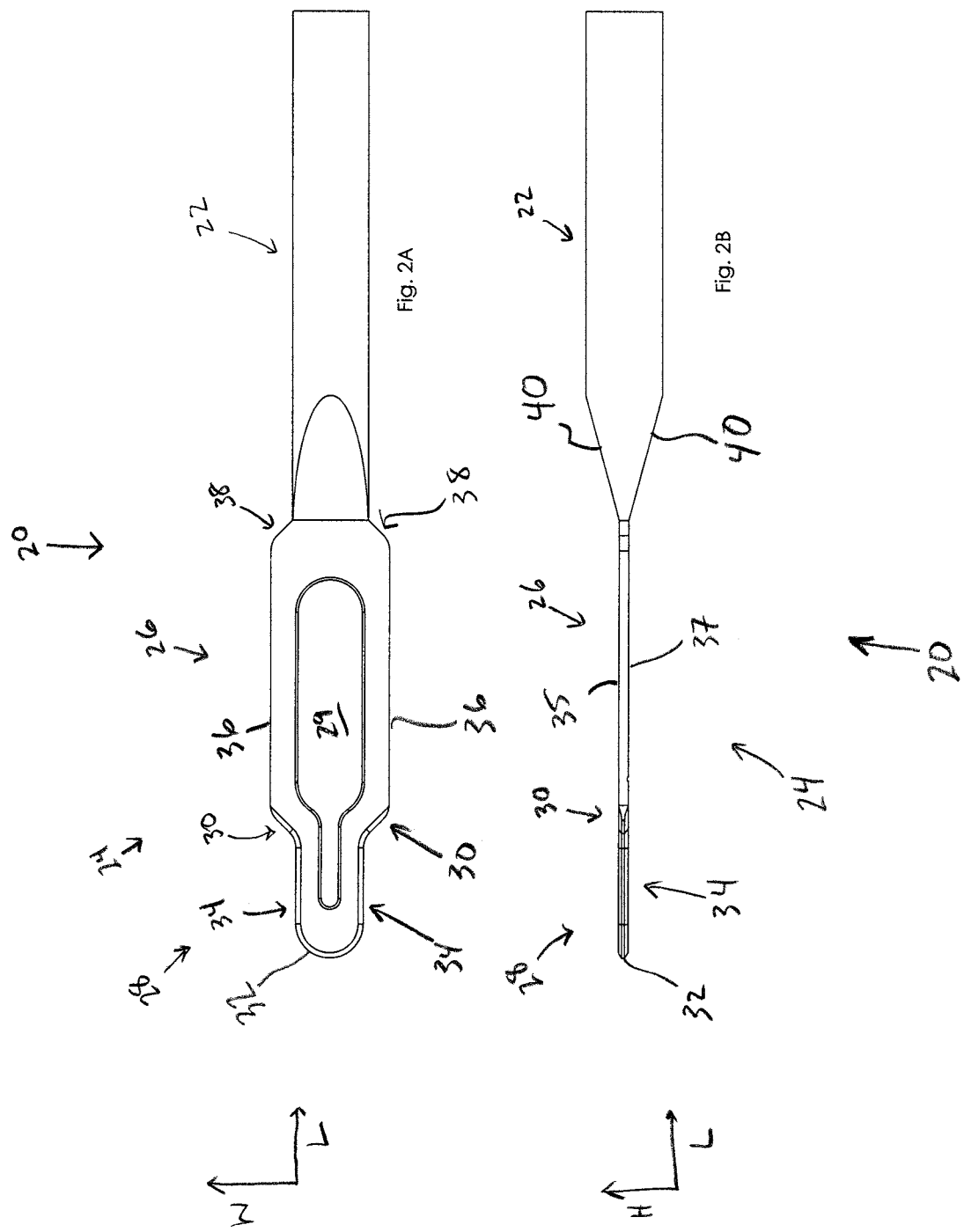

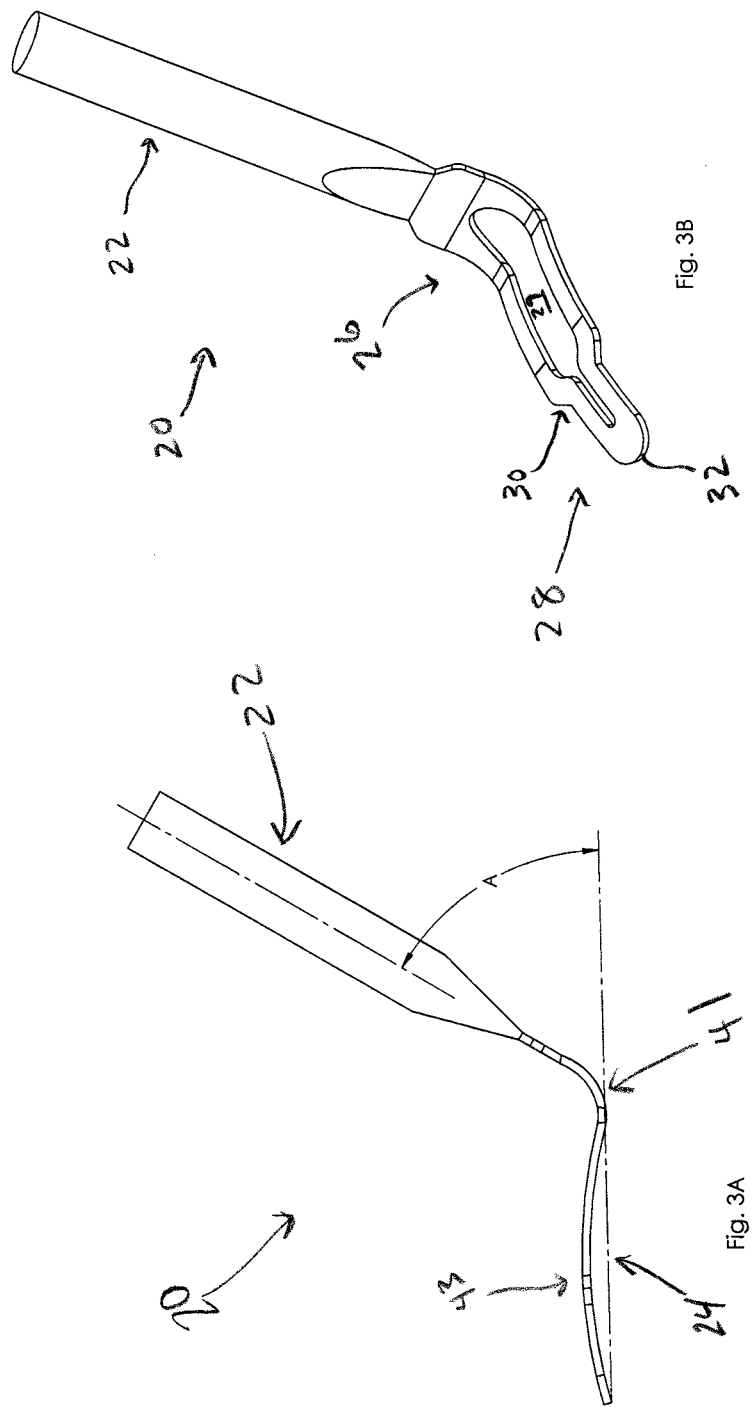

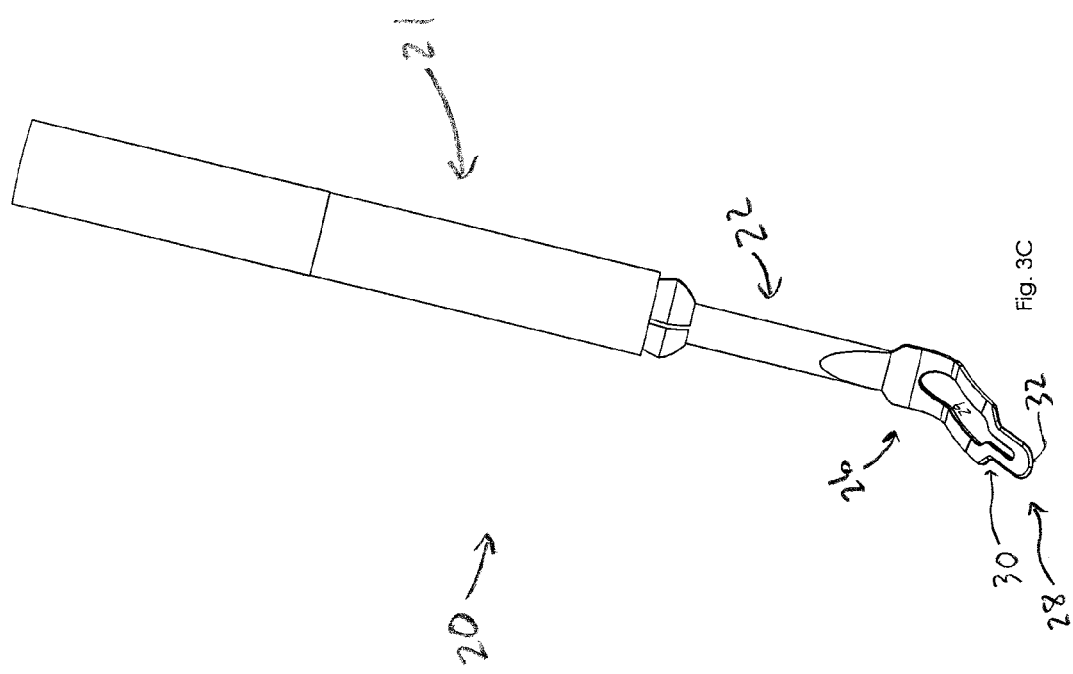

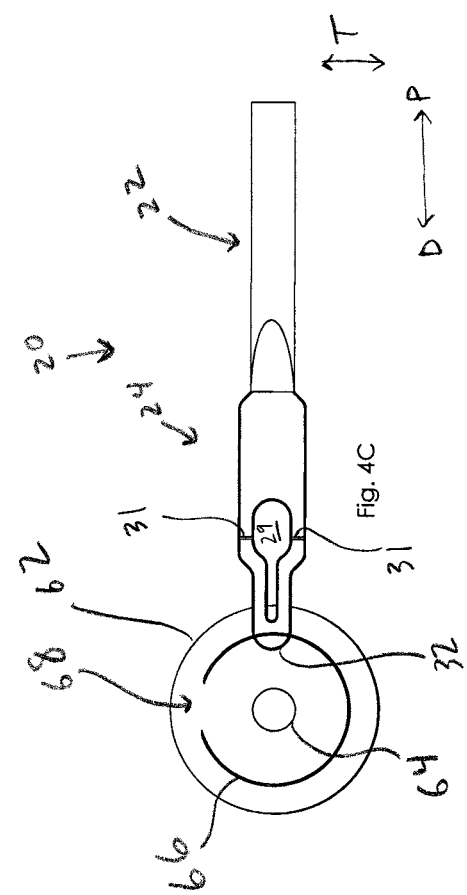

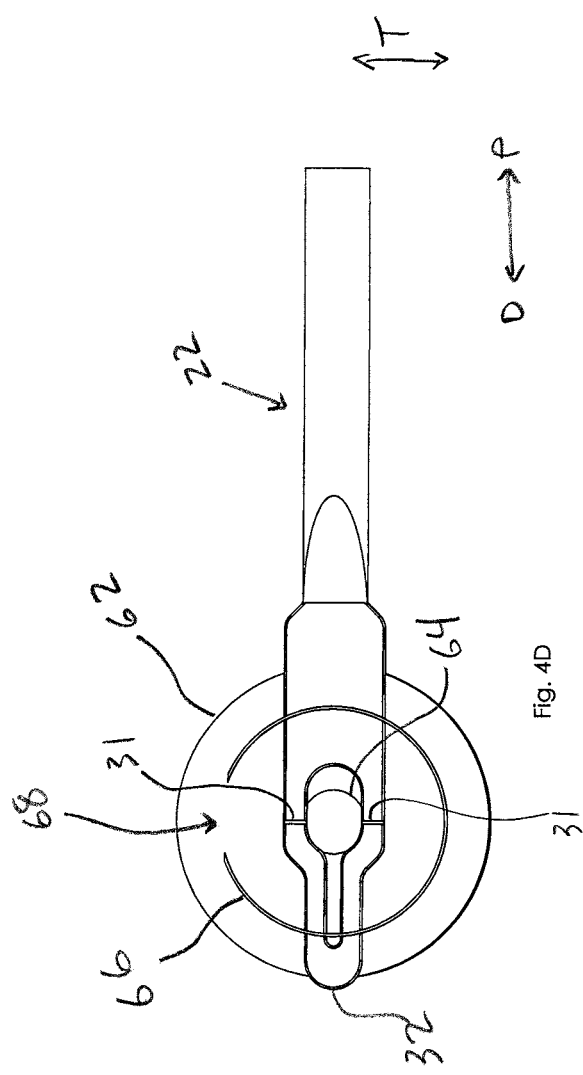

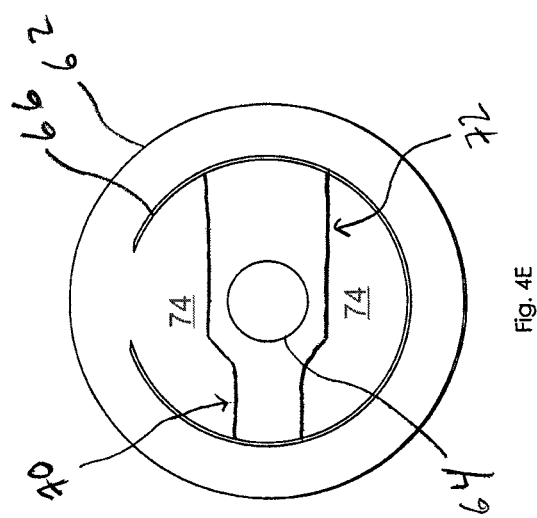

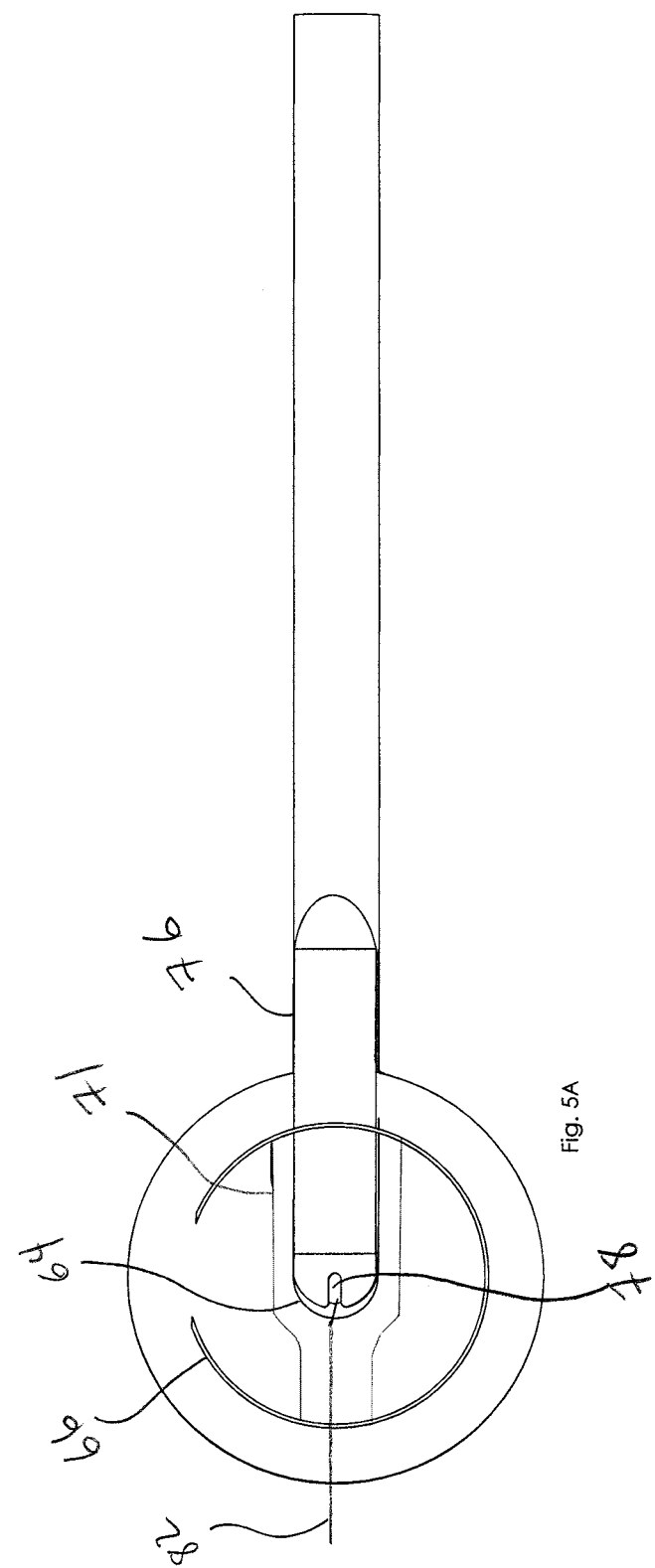

METHODS AND DEVICES FOR FORMING CORNEAL CHANNELS

INCORPORATION BY REFERENCE

All publications and patent applications mentioned in this specification are herein incorporated by reference to the same extent as if each individual publication or patent application was specifically and individually indicated to be incorporated by reference herein.

BACKGROUND OF THE INVENTION

Corneal implants have been developed to correct refractive errors in the eye such as presbyopia, myopia, and hyperopia. Corneal implants have traditionally been implanted within the cornea either by positioning the implant within a pocket created in the cornea, or by lifting a flap created in the cornea, positioning the implant on the exposed corneal bed, and placing the flap back over the implant. A corneal pocket can be created with a blade-like spatula, which is advanced into corneal tissue to dissect the tissue and thereby create a pocket. A corneal implant can thereafter be positioned into the corneal pocket. Known dissecting blades and methods of use are not, however, configured to easily create a corneal channel or pocket to receive a corneal implant.

Corneal flaps can be created using mechanical microkeratomes or femtosecond lasers, which create a series of small, closely arranged bubbles within the cornea. The bubbles are not, however, completely connected, and corneal tissue (sometimes referred to as "tags") remain between the bubbles. To fully separate the flap to expose the corneal bed, the tags must be broken. When forming the flap, a region along the periphery of the flap is left intact to create a flap hinge. After the flap is lifted to expose the corneal bed, a corneal implant can then be positioned on the corneal bed. The flap is thereafter positioned back down over the corneal implant.

Devices and methods of use are needed to more easily create corneal channels.

SUMMARY OF THE INVENTION

One aspect of the disclosure is an instrument for creating a channel in a patient's cornea. The instrument includes a handle portion, and an elongate channel portion extending from the handle portion and adapted to break corneal tags, wherein the channel portion comprises a window therethrough.

In some embodiments the channel portion comprises a distal end with a beveled surface, which can be a double beveled surface, adapted to break corneal tags. The distal end can be curved, and the channel portion can include substantially straight side edges extending from the curved distal end. The substantially straight side edges can be double-beveled.

In some embodiments the channel portion comprises a first channel portion with a first width and a second channel portion with a second width, wherein the first width is less than the second width. The first channel portion can be disposed distal relative to the second channel portion. The channel portion can include a transition portion between the first channel portion and the second channel portion, wherein the transition portion has a width that transitions from the first width to the second width. The window can extend through the second channel portion, or the window can extend through the second channel portion and the first channel portion. The window can have a distal window portion with a first width and a proximal window portion with a second with, wherein the first width is less than the second width, and wherein the distal window portion extends through at least a portion of the first channel portion and the proximal window portion extends through at least a portion of the second channel portion.

In some embodiments the channel portion comprises a distal portion with a beveled edge and a proximal portion that does not have a beveled edge.

In some embodiments the channel portion has a curved configuration when viewed from the side. The channel portion can have a first bend and a second bend to create a generally S-bend configuration when viewed from the side In some embodiments the channel portion comprises a marker adapted to indicate the channel portion's position relative to a pupil.

One aspect of the disclosure is an instrument for creating a channel in a patient's cornea. The instrument includes a handle portion, and an elongate channel portion extending from the handle portion adapted to break corneal tags, wherein the channel portion comprises a distal portion with a first width and a proximal portion with a second with, wherein the first width is less than the second width.

In some embodiments the distal portion comprises a double-beveled edge adapted to break corneal tags. The distal portion can comprise a curved distal end with the double-beveled edge. The distal portion can comprise an intermediate region extending from the distal end, wherein the intermediate region has a double-beveled edge.

In some embodiments the channel portion comprises an opening therethrough. The opening can extend through at least a portion of the proximal portion. The opening can also extend through at least a portion of the distal portion.

In some embodiments the channel portion comprises a marker adapted to indicate the channel portion's position relative to a pupil.

One aspect of the disclosure is method of creating a channel in a patient's cornea, including disrupting corneal tissue to create a first region of the cornea defined by a plurality of corneal tags; and creating a corneal channel within the first region of the cornea by breaking a first portion of the plurality of corneal tags, wherein the first region is larger than the cornea channel, and wherein the method does not comprise lifting corneal tissue.

In some embodiments creating the corneal channel comprises advancing a channel instrument into the first region to break the first portion of the plurality of corneal tags. The advancing step can comprise advancing the channel instrument from a first side of the first region to a second side of the first region to create a corneal channel that extends from the first side to the second side of the first region. The advancing step can comprise advancing the channel instrument along a substantially linear path from a first side of the first region to a second side of the first region.

In some embodiments the method further comprises creating a first side cut and a second side cut at a periphery of the first region, wherein the first and second side cuts each subtend an angle less than about 90 degrees.

In some embodiments creating a corneal channel creates a channel with a first portion with a first width and a second portion with a second width, wherein the first width is different than the second width.

In some embodiments disrupting corneal tissue comprises disrupting corneal tissue with a femtosecond laser to create a first region of the cornea defined by a plurality of corneal tags.

In some embodiments the method further comprises comprising creating a peripheral side cut that does not have a generally circular shape.

In some embodiments the method further comprises positioning a corneal implant within the corneal channel. Positioning the corneal implant can include positioning the cornea implant substantially within the boundaries of a pupil.

In some embodiments the method further comprises advancing a corneal implant through the corneal channel within a delivery tool, and implanting the corneal implant within the corneal channel. 37. Creating the cornea channel can comprise creating a corneal channel extending from a first side of the first region to a second side of the first region, and wherein advancing the corneal implant comprises advancing the corneal implant through the corneal channel within the delivery tool from the first side of the region. 38. Implanting the corneal implant can comprise advancing a removal tool into the corneal channel from the second side of the first region and removing the implant from the delivery tool with the removal tool.

In some embodiments creating the corneal channel comprises advancing a channel instrument from a first side of the first region through corneal tissue without advancing the channel instrument out of a second side of the first region.

One aspect of the disclosure is a method of creating a channel in a patient's cornea. The method includes disrupting corneal tissue with a laser to create a first region of the cornea comprising a plurality of corneal tags; and creating a corneal channel within the first region of the cornea by advancing a channel instrument into the first region from a first side of the first region to break a first portion of the plurality of corneal tags without breaking a second portion of the plurality of corneal tags, wherein the method does not comprise lifting corneal tissue.

In some embodiments the advancing step comprises advancing the channel instrument along a substantially linear path in the first region to create a substantially linear-shaped channel.

In some embodiments the advancing step comprises creating a channel with a first portion with a first width and a second portion with a second width, wherein the first width is different than the second width.

In some embodiments the method further comprises positioning a corneal implant within the corneal channel.

In some embodiments creating a channel comprises advancing a channel instrument into the first region from a first side of the first region and out a second side of the first region to break a first portion of the plurality of corneal tags without breaking a second portion of the plurality of corneal tags.

In some embodiments the method further comprises creating a peripheral side cut at a periphery of the first region that subtends an angle less than about 90 degrees.

One aspect of the disclosure is a method of correcting a subject's corneal refractive error, comprising: performing a LASIK procedure on the subject, wherein the LASIK procedure comprises creating a corneal flap, lifting the corneal flap, remodeling corneal tissue, and repositioning the flap; and advancing a channel instrument under the flap created during the LASIK procedure to create a channel in the cornea, wherein the channel creation step is performed after performing the LASIK procedure.

In some embodiments the method further comprises implanting a corneal implant within the channel created in the cornea.

In some embodiments the advancing step comprises advancing the channel instrument along a substantially linear path from a first side of the cornea to a second side of the cornea to create a substantially linear channel.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIGS. 2A-3C illustrate an exemplary corneal channel instrument.

FIGS. 4A-4E illustrate an exemplary method of creating a corneal channel.

FIGS. 5A-5B illustrate an exemplary method of positioning a corneal implant within a corneal channel.

DETAILED DESCRIPTION OF THE INVENTION

The disclosure generally refers to devices and methods for creating channels within corneal tissue. A corneal "channel" as used herein can include what is generally known as a corneal "pocket," and in some instances may include characteristics not generally associated with corneal pockets. In some embodiments a corneal implant is positioned within the corneal channel after the channel is created. In some embodiments the corneal implant is a corneal inlay.

Figure 1:
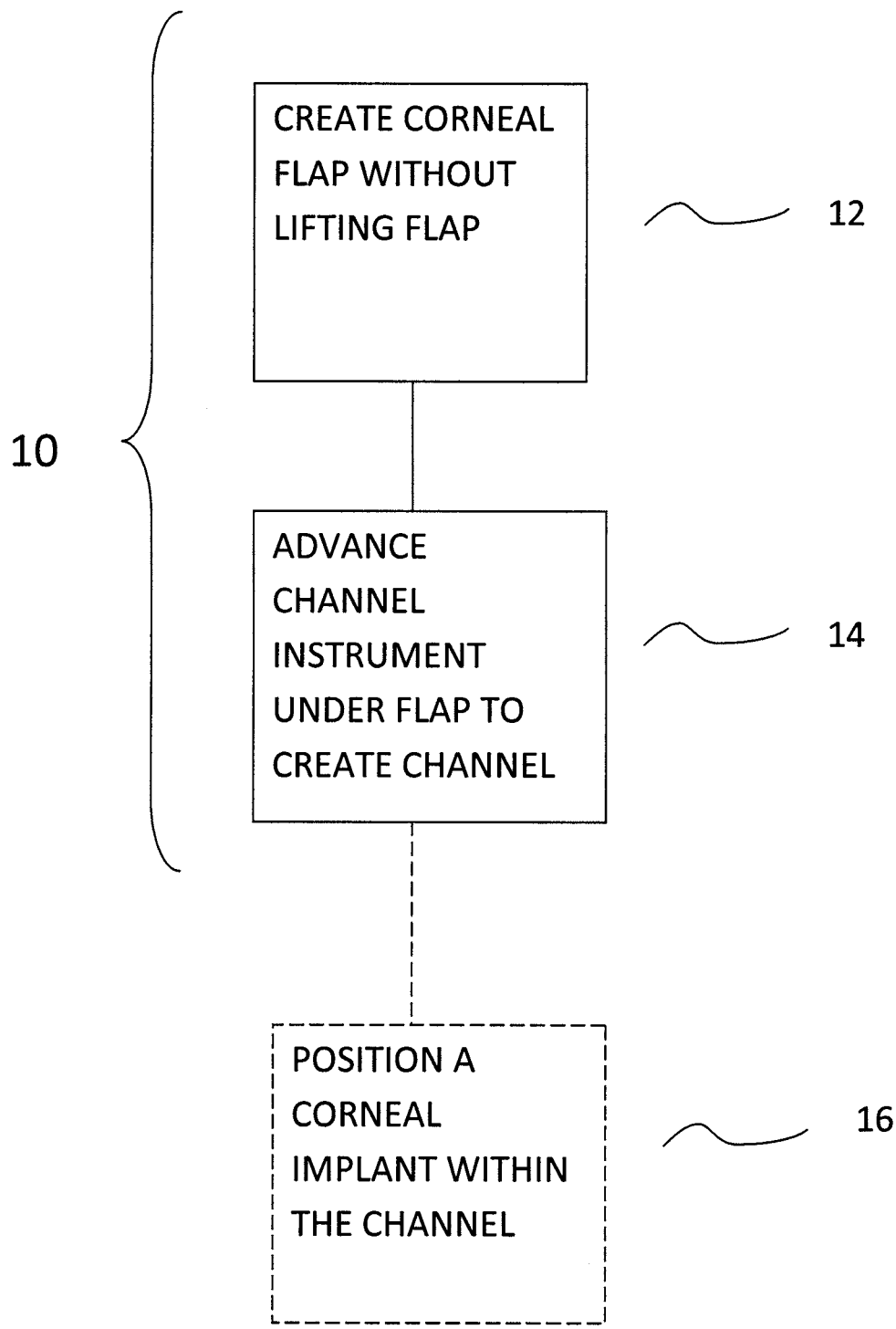
FIG. 1 describes an exemplary method of creating a corneal channel.

FIG. 1 illustrates an exemplary method 10 of creating a corneal channel. Method 10 includes the step of creating a corneal flap by disrupting corneal tissue, but without lifting the flap 12. Creating the corneal flap by corneal tissue disruption can be performed with a laser, such as a femtosecond laser (e.g., Intralase®). Application of the femtosecond laser to the corneal tissue creates small, closely arranged bubbles within the cornea. Upon the application of the femtosecond laser, the bubbles remain separated by corneal tissue (sometimes referred to as "tags"). Step 12 can be considered similar to the initial application of a laser during an IntraLASIK procedure. In some procedures, such as LASIK or the implantation of a corneal implant under a corneal flap, the procedure also includes, however, breaking all of the tags created in the initial step and lifting the flap to expose the corneal bed. In step 12, however, the flap that is created by disrupting the cornea tissue is not lifted, and the tags remain fully intact.

After the flap is created (but without lifting the flap) in step 12, an instrument adapted to create a corneal channel is advanced under a selected portion of the flap at step 14 to create a corneal channel. In step 14, the channel-maker instrument is advanced under the flap and across at least a portion of the cornea to gently break a selected portion of the tags created during step 12. In general, the channel-maker instrument does not disrupt all of the tags, but rather is advanced through a selected portion of the cornea to create a corneal channel. Creating the channel according to method 10 therefore does not disrupt all of the tags, as would occur when lifting a flap. Creating a corneal channel according to step 14 is therefore generally less invasive than lifting a corneal flap.

Method 10 can also include an optional step, between steps 12 and 14, of advancing a starter channel device, such as a spatula (e.g., a MacRae spatula) or similar device, under the flap to create a starter channel in the cornea. The starter channel is generally narrower than the corneal channel created at step 14, and thus the starter channel device can be narrower than the channel maker instrument. Creating a starter channel can reduce the resistance from the tags as the channel maker instrument is advanced under the flap to create the channel geometry during step 14. In some specific embodiments a MacRae spatula that is about 0.75 mm wide can be advanced under the flap created in step 12 to create a starter channel before step 14.

Method 10 optionally includes the step of positioning a corneal implant within the channel 16 after the corneal channel is created in step 14. For example but without limitation, after the corneal channel is created, a corneal inlay can be positioned within the channel to correct one or more visual errors. Examples of corneal implants that can be positioned within a corneal channel as described herein can be found in U.S. Pat. Nos. 5,196,026; 5,336,261; 5,391,201; 4,607,617; 4,624,669; 6,102,946; 6,221,067; 6,361,560; 6,607,556; 6,623,522; 6,626,941; 6,855,163; 5,123,921; U.S. Patent Application Publication No. 2001/0027314; U.S. Pat. No. 6,849,090; U.S. Patent Application Publication No. 2005/0246015; U.S. Patent Application Publication No. 2005/0246016; U.S. Patent Application Publication No. 2007/0203577; U.S. Patent Application Publication No. 2008/0262610, all of which are incorporated herein by reference.

FIGS. 2A-3B illustrate an exemplary corneal channel instrument 20. FIG. 2A is a top view of instrument 20 while FIG. 2B is a side view. FIGS. 2A and 2B illustrate the instrument before a channel portion of the device is reconfigured, as is described below. FIG. 3A shows a side view of instrument 20 after the channel portion is reconfigured, while FIG. 3B shows a perspective view of the instrument shown in FIG. 3A.

Corneal channel instrument 20 includes handle portion 22 and channel portion 24. The handle portion can be generally adapted to be handled by a user to control the positioning of channel portion 24, or alternatively, as shown in FIG. 3C, handle portion 22 is adapted to be inserted into a designated handle element 21. In FIG. 3C, handle element 21 is a chuck handle for improved handling. Handle portion 22 and channel portion 24 can be manufactured from a single piece of material, or can be two or more pieces of material coupled together to form instrument 20. If formed from two or more pieces of material, handle portion 22 and channel portion 24 can be the same type of material or they can be different types of material. In one exemplary embodiment, the channel instrument is machined from stainless steel, and the channel portion is machined to be substantially flat, such as is shown in the side view in FIG. 2B. The channel instrument can also be made from titanium.

In FIGS. 2A-3B, channel portion 24 includes proximal region 26 and distal region 28. Distal region 28 comprises at least one edge that is adapted to gently disrupt the corneal tags to create the channel. The width of proximal region 26 is greater than the width of distal region 28. An inner surface of both proximal region 26 and distal region 28 of channel portion 24 defines window or opening 29 (see FIG. 2A) that extends through both proximal region 26 and distal region 28. Opening 29 is configured to allow a user to visualize portions of the eye posterior to the channel instrument during the channel-creation procedure. In some embodiments the channel portion is machined to include at least one opening, although more than one distinct opening can be created in the channel portion.

In FIGS. 2A-3B, distal region 28 of channel portion 24 comprises distal end 32, intermediate region 34, and transition region 30, all of which are shown with a double-beveled edge (the double-beveled edge of distal end 32 can be more clearly seen in FIG. 2B). Distal end 32 is generally curved, as can be seen in FIGS. 2A and 3B. In the top-view of FIG. 2A, distal end 32 has a generally semi-circular edge shape. Intermediate region 34 is shown with generally straight and substantially parallel double-beveled edges, while transition region 30 has both curved and straight double-beveled edges. Proximal region 26 of channel portion 24 has substantially straight, flat edges, except in proximal transition region 38. Handle portion 22 extends proximally from transition region 38. Handle portion 22 includes beveled surfaces 40. Channel portion 24 is also formed with top surface 35 and bottom surface 37, which are generally flat and generally parallel to one another, as can be seen in FIG. 2B.

As shown in the side-view of FIG. 2B, channel portion 24 is formed in a substantially flat configuration, and is thereafter reconfigured into the configuration shown in FIGS. 3A and 3B. Alternatively, the entire device, including the channel portion, can be molded out of plastic. Channel portion 24 is reconfigured to include proximal bend 41 and distal bend 43, together which provide channel portion 24 with a general S-bend shape when viewed from the side (see FIG. 3A). Instrument 20 is reconfigured with the exemplary configuration shown in FIGS. 3A and 3B to allow a user to easily grasp handle portion 22 and advance channel portion 24 under corneal tissue, as is described in more detail below. The curvature of bend 43 is similar to the curvature of the anterior surface of the cornea to make it easier to advance the instrument through the cornea.

In FIGS. 2A and 2B, the coordinate "W" describes the width dimensions of the elements of instrument 20, while the "L" coordinate describes the length dimensions. Similarly, in FIG. 2B the "H" dimension describes the height dimensions of the components, and the L coordinate describes the length dimensions. In FIGS. 2A and 2B, the width of distal end 32 and intermediate region is about 2 mm. The width of proximal portion 26 is about 3.5 mm. The width/diameter of handle portion 22 is about 2.3 mm. The length of channel portion 24 (in the flat configuration of FIGS. 2A and 2B) is about 13 mm. The length from the distal-most portion of distal end 32 to the proximal end of transition region 30 is about 4.5 mm. The length of proximal portion 26 is about 8.5 mm. The length of the opening 29 is about 9 mm. The height of channel portion 24 is about 0.35 mm. The angle of the bevel is about 30 degree relative to the longitudinal axis of the device as shown in FIG. 2B. When channel portion is reconfigured to the configuration shown in FIGS. 3A and 3B, the radius of curvature of bend 43 is about 18 mm. Angle "A" shown in FIG. 3A is about 60 degrees. The dimensions and angles described above are merely exemplary and are not limiting.

The specific configuration and dimensions of channel portion 24 in FIGS. 2A-3B are not meant to be limiting for a channel instrument described herein. For example, distal region 28 and proximal region 26 can have substantially the same width. Opening 29 could have a substantially uniform width across distal and proximal regions 28 and 26. All of the edges of distal region 28 need not all have beveled edges, or if they do, they need not be double-beveled edges. These are simply examples of how the embodiment in FIGS. 2A-3B is not intended to be limiting to the channel instruments described herein.

Figure 4A:
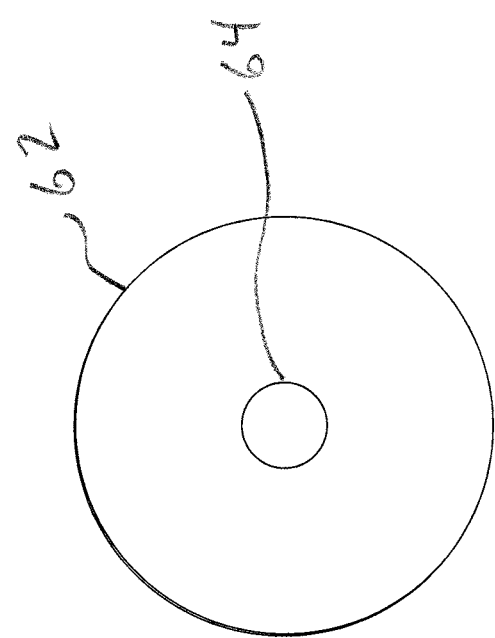
Figure 4B:
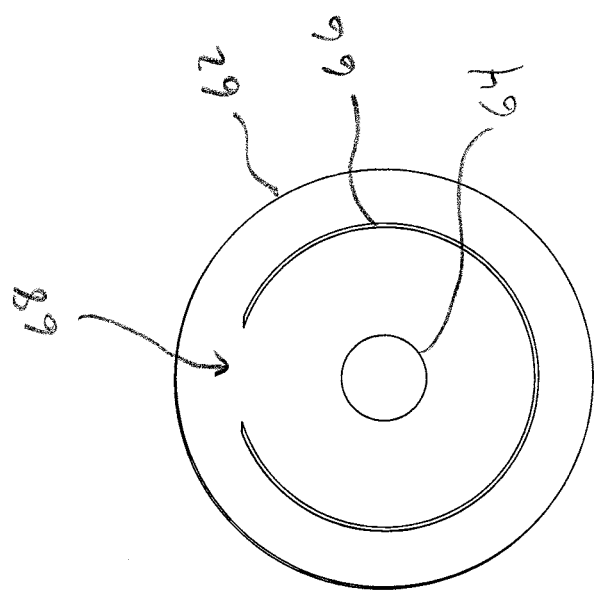

FIGS. 4A-4E are top views illustrating an exemplary method of creating a corneal pocket in a patient's cornea using the exemplary channel instrument shown in FIGS. 2A-3B. FIG. 4A illustrates a portion of cornea 62 and shows pupil 64. In FIG. 4B, corneal flap 66 with hinge 68 is first created with a laser, such as a femtosecond laser. In FIG. 4B, flap 66 has not been lifted, however, and tags remain between the bubbles as discussed above. Next, as shown in FIG. 4C, distal end 32 of instrument 20 is advanced in the direction "D" from a first side of flap 66 and under the flap, as shown in FIG. 4C. The double-beveled edge on the distal end 32 (and optionally on intermediate region 34 and transition region 30), which is not a "sharp" edge in this embodiment, reduces the effort needed to advance the instrument across the cornea and through the tags. The thin profile of the channel portion also helps reduce the effort needed to advance the instrument across the cornea. Instrument 20 continues to be advanced across the entire flap, breaking the tags in a selected region, until marker 31 is substantially aligned with the patient's pupil, as shown in FIG. 4D. Additionally, pupil 64 can be visualized through opening 29 in instrument 20. Distal end 32 has been, as shown in FIG. 4D, advanced out of the flap on the other side relative to the entry side. Advancing instrument 20 through the cornea breaks the tags and creates a corneal channel through corneal tissue extending from one side of the flap to the other side. Instrument 20 is thereafter removed from the cornea in the direction "P," creating a corneal channel comprising distal channel portion 70 and proximal channel portion 72, as is shown in FIG. 4E. Distal channel portion 70 has a width that is less than the width of proximal channel portion 72. Regions 74 represent regions of the flap in which the tags remain intact and are not broken by instrument 20. Stated alternatively, the channel does not extend through regions 74 and is not made in regions 74. When viewed from above, the area defined by the channel is therefore less than the area in which the corneal tissue is disrupted in the first step of the procedure.

As can be seen in FIG. 4E, the channel created in cornea 62 has the same general shape as instrument 20. That is, the shape of the channel to be created can be adjusted by changing the dimensions and shape of the channel portion. For example, the width of the channel can be substantially constant along the length of the channel if the channel portion of the instrument has a substantially constant width.

As can be seen in FIG. 4E, the arcs defined by the channel entrance and the channel exit each subtend an angle less than 360 degrees. In this embodiment the entrance and exit each subtend an angle less than about 60 degrees (the figure is not necessarily drawn to scale). Thus, the method does not comprises breaking tags in the entire region of the cornea flap or lifting the flap, as would be done during some procedures, such as a LASIK procedure. The entrance and exit (or just the entrance as shown in the embodiment in FIGS. 9-11 below) can each be less than about 270 degrees, less than about 180 degrees, less than about 90 degrees, less than about 60 degrees, less than about 30 degrees, or less than about 15 degrees. The lower limit on the entrance size can be established to be able to accommodate a corneal implant inserter device, as described below.

Figure 5B:
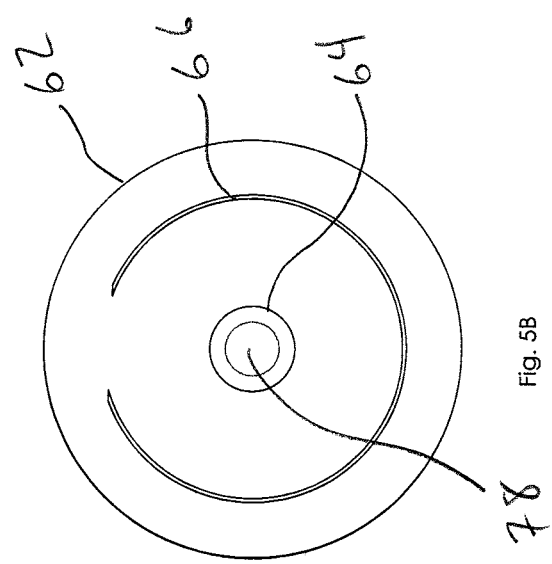

FIGS. 5A and 5B illustrate an exemplary optional step of implanting a corneal implant within the cornea, and specifically within the channel created during the exemplary method shown in FIGS. 4A-4E. In FIG. 5A, corneal implant delivery tool 76 is advanced in the direction "D" into channel 71 (not shown in phantom for clarity) created by the channel instrument. Delivery tool 76 has corneal implant 78 retained therein in a distal region of delivery tool 76. A portion of implant 78 can be seen in the top-view of FIG. 5A through a slot in the top of delivery tool 76. Removal tool 82 is positioned into channel 71 where the channel instrument exited during the method shown in FIGS. 4A-4E. In FIG. 5A, delivery tool 76 is advanced through channel 71 in direction D, while removal tool 82 is advanced through channel 71 in direction P. Delivery tool 76 is advanced until the implant 78 is positioned over and within the boundaries of the pupil (as viewed from above), as is the position shown in FIG. 5A. To remove implant 78 from delivery tool 76, removal tool 82 is advanced in the P direction until the tip of the removal tool contacts the portion of implant 78 that can be seen through the slot in delivery tool 76. Slight pressure from removal tool 82 on the anterior surface of implant 78 will maintain the position of implant 78 as delivery tool 76 is withdrawn in the P direction, which withdraws tool 76 from the patient's eye. Removal tool 82 is then withdrawn in the D direction from the patient's eye, leaving implant 78 positioned within the corneal channel, as shown in FIG. 5B. In some embodiments, such as is described in more detail in U.S. Pat. No. 6,102,946; U.S. Pat. No. 6,361,560; U.S. Pat. No. 6,626,941; U.S. Patent Application Publication No. 2007/0203577; U.S. Patent Application Publication No. 2008/0262610; and U.S. Patent Application Publication No. 2009/0198325 (all of which are incorporated herein by reference), implant 78 is positioned at a depth within the cornea to produce a shape change in the anterior surface of the cornea. In some embodiments the implant is a corneal inlay with a diameter between about 1 mm and about 4 mm in diameter. In the embodiments shown in FIGS. 5A and 5B, the implant is retained within the delivery tool in an unstressed configuration.

The channel can be created at almost any depth within the cornea. In some embodiments the channel is created at a depth of less than about 50% of the cornea. In some embodiments the channel is created at a depth of less than about 45% of the cornea. In some embodiments the channel is created at a depth of less than about 40% of the cornea. In some embodiments the channel is created at a depth of less than about 35% of the cornea. In some embodiments the channel is created at a depth of less than about 30% of the cornea. In some embodiments the channel is created at a depth of less than about 25% of the cornea. In some embodiments the channel is created at a depth of less than about 20% of the cornea. In some embodiments the channel is created at a depth of less than about 10% of the cornea. In some embodiments the channel is created at a depth of more than 50% of the cornea. In some embodiments the channel is created at a depth of more than 75% of the cornea.

In some embodiments the channel is made at a depth of less than 50% of the cornea, the implant has an index of refraction substantially the same as that of the cornea tissue, the implant has a diameter of about 1 mm to about 3 mm, and is adapted, once implanted, to change the curvature of the anterior surface of the cornea to create a near vision region in the center of the cornea and a distance vision region peripheral to the near vision region.

In some embodiments the channel is made at a depth of greater than 50% of the cornea, the implant has an index of refraction different than that of the cornea, has a diameter between about 1 mm and about 4 mm, and corrects a visual error by creating a refractive interface between corneal tissue and the implant within the cornea.

Examples of delivery tools that can be advanced into corneal channels described herein are described in U.S. Patent Application Publication No. 2008/0243138, the disclosure of which is incorporated by reference herein.

Figure 6:
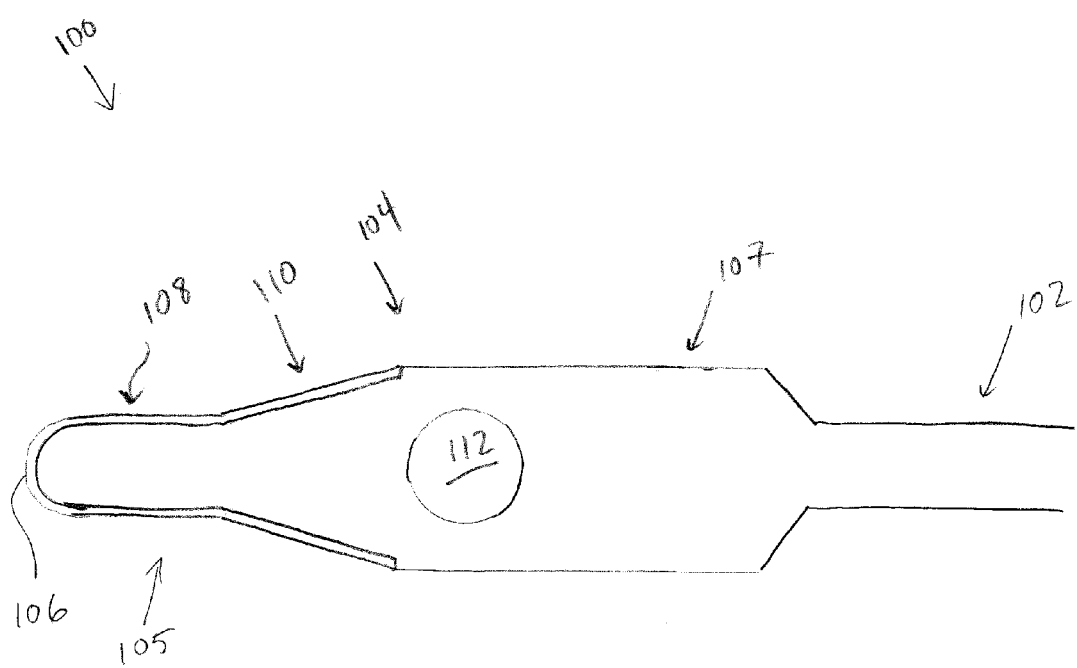
FIG. 6 illustrates an exemplary corneal channel instrument.

FIG. 6 illustrates a top view of an exemplary corneal channel instrument. Instrument 100 includes handle portion 102 and channel portion 104. Channel portion 104 includes distal region 105 and proximal region 107. Distal region 105 includes distal end 106, intermediate region 108, and transition region 110. Transition region 110 extends between intermediate region 108 and proximal portion 107. Distal end 106, intermediate region 108, and transition region 110 have double-beveled edges as in the embodiment in FIGS. 2A-3B. An inner surface of channel portion 104 defines window or opening 112 that extends only through proximal region 107, and not into distal region 105. Similar to other embodiments herein, channel portion 104 can initially be created flat and then reconfigured into a generally curved configuration.

Figure 7:
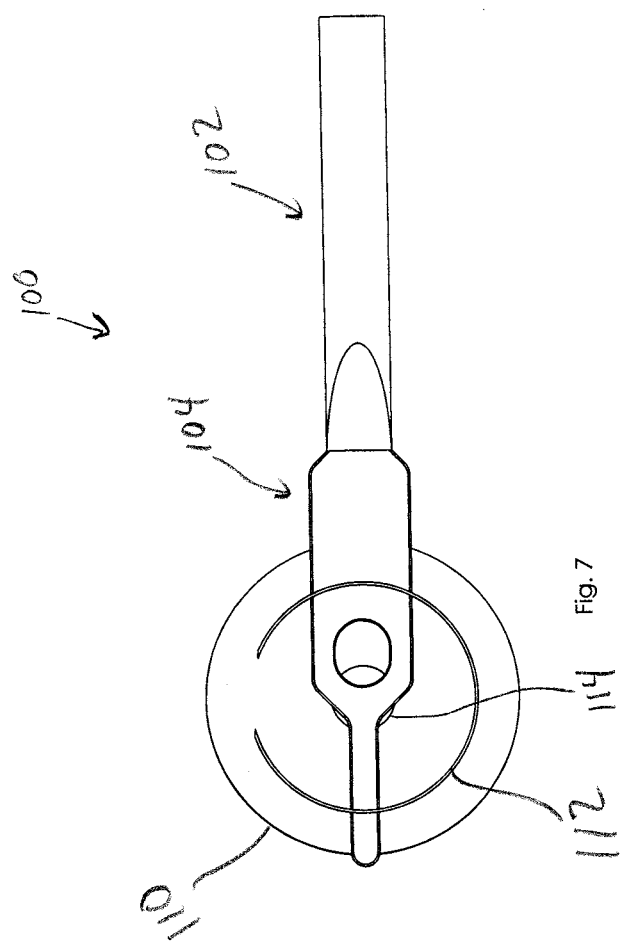
FIG. 7 illustrates an exemplary method of creating a corneal channel.

FIG. 7 illustrates a portion of an exemplary method of advancing instrument 100 under flap 112 similar to the method shown in FIGS. 4A-4E. The distal end of the channel portion is advanced under flap 112 (without lifting the flap) from one side. The channel portion is advanced through the cornea to create a corneal pocket. The opening or window allows a user to visualize pupil 114 for proper creation of the channel. After instrument 100 is removed from the cornea, a corneal implant can then be positioned in the corneal channel.

Figure 8:
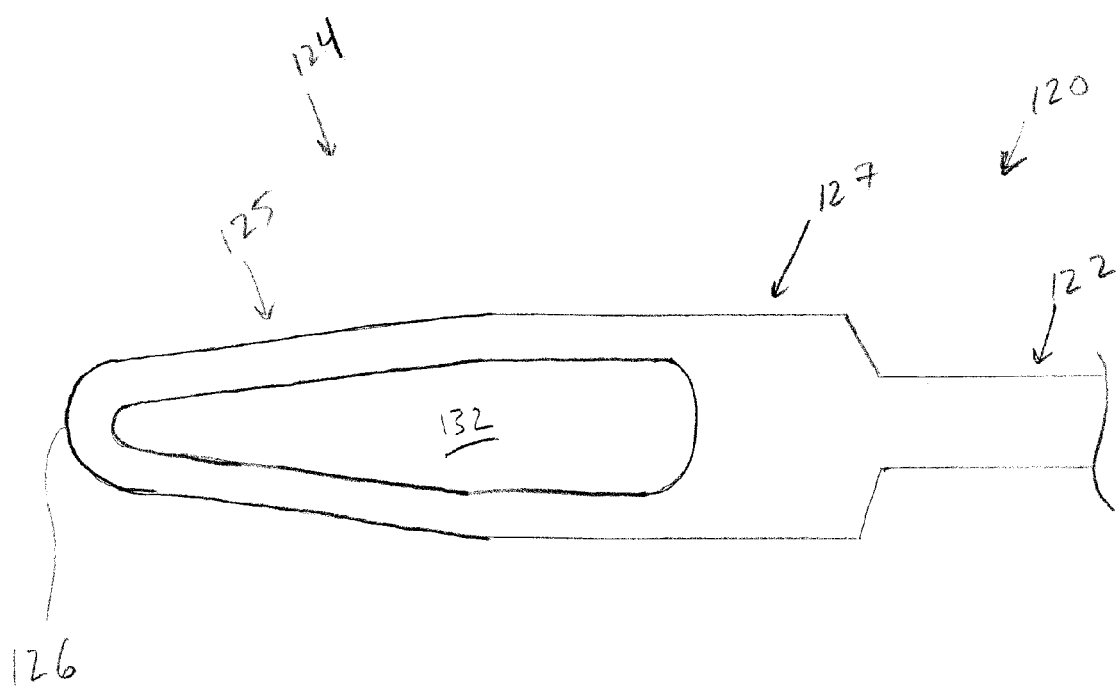
FIG. 8 illustrates an exemplary corneal channel instrument.

FIG. 8 illustrates a top view of an exemplary embodiment of a corneal channel instrument. Instrument 120 includes handle portion 122 and channel portion 124. Channel portion includes distal end 126 and intermediate region 125. The distal end and intermediate region have double-beveled edges to ease the insertion of the instrument through the cornea. An inner surface of channel portion 124 defines opening or window 132, which can alternatively extend only through proximal region 127. The embodiment in FIG. 8 can be used to create a corneal channel as described herein.

Figure 9:
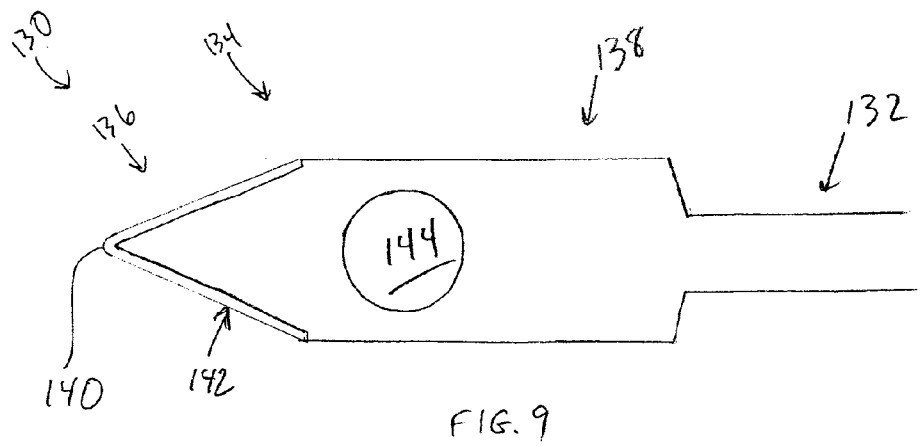
FIG. 9 illustrates an exemplary corneal channel instrument.
Figure 10:
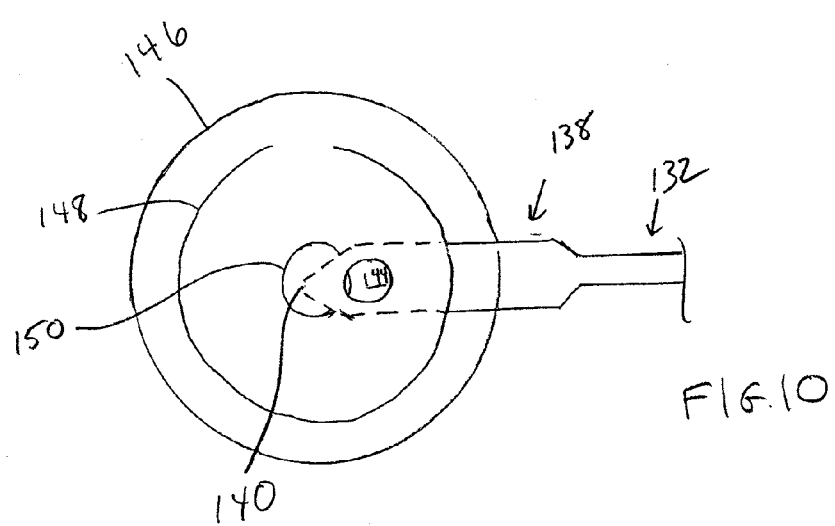
FIG. 10 illustrates an exemplary method of creating a corneal channel.
Figure 11:
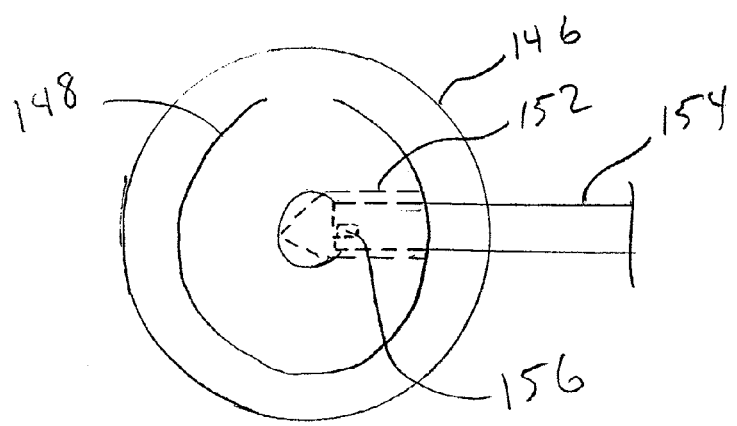
FIG. 11 illustrates an exemplary method of positioning a corneal implant within a corneal channel.

FIG. 9 illustrates a top view of an exemplary embodiment of a corneal channel instrument. Instrument 130 includes handle portion 132 and channel portion 134. Channel portion 134 includes distal region 136 and proximal region 138. Distal region includes distal end 140 and intermediate region 142. Distal end 140 and intermediate region 142 have beveled edges, and an inner surface of channel portion 134 defines opening 144. FIG. 10 illustrates instrument 130 from FIG. 9 advanced under flap 148 until distal end 140 is positioned roughly in alignment with the pupil, but this is not limiting and depends more on the shape of distal region 136. The distal end of instrument 130 is not advanced out of the other side of the flap as occurs in some embodiments herein. After instrument 130 is removed from the cornea, channel 152 that is created by instrument 130, as shown in FIG. 11, does not extend from one side of the flap to the other side of the flap. In this embodiment channel 152 extends about half-way across the flap. Because the channel does not extend all the way across the flap to the other side, implant delivery tool 154 is configured to be able to delivery implant 156 into the channel without the need for a removal tool advanced from the other side of the flap. Exemplary delivery tool 154 has a lumen in fluid communication with the distal end of delivery tool, in which implant 156 is retained. The lumen allows a delivery material, such as a fluid, to be advanced distally down the lumen and displace implant 156 from within delivery tool 156 and into channel 152. Similar to the embodiment shown in FIG. 5B, corneal implant 156 can be positioned substantially within the boundaries of the pupil and can be adapted to modify the curvature of the anterior surface of the cornea. An exemplary delivery tool with a fluid lumen is described in U.S. Patent Application Publication No. 2008/0243138, which is incorporated by reference herein. Optionally, after delivery tool 154 is removed from the cornea, a positioning instrument such as the removal tool described in reference to FIG. 5A (not shown) can be advanced into channel 152 and can be used to adjust the positioning of implant 156 in channel 152 if necessary.

Figure 12:
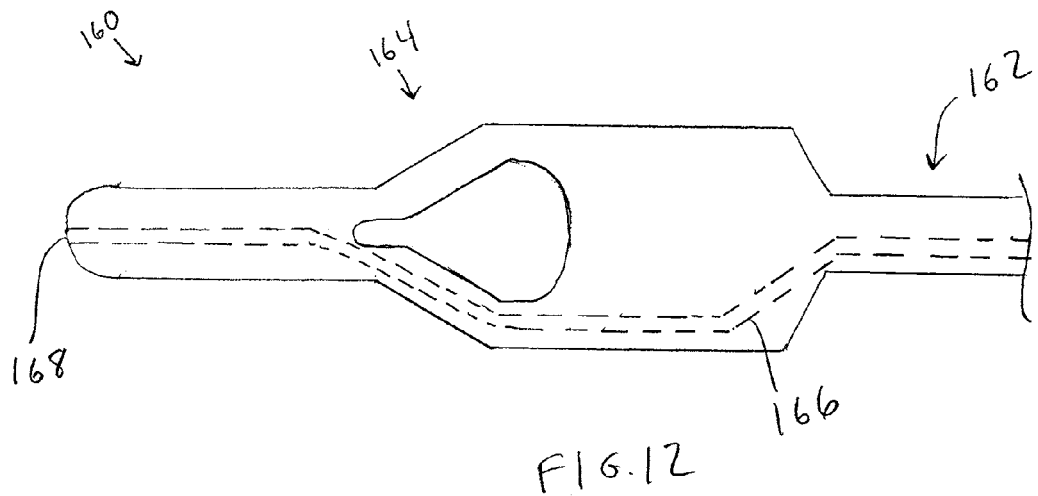
FIG. 12 illustrates an exemplary corneal channel instrument.

FIG. 12 shows a top view of an exemplary embodiment of a channel instrument. Instrument 160 includes handle portion 162 and channel portion 164. Instrument 160 includes lumen 166 extending from handle portion 162 to distal port 168 and is configured to allow a fluid, such as a liquid (e.g., saline) to be advanced down lumen 166 and out of distal port 168. The fluid can be advanced out of distal port 168 while the instrument is being advanced under the flap to lubricate the instrument and decrease the corneal resistance to the instrument. In one embodiment handle portion 162 includes a port to receive a fluid delivery device, such as a syringe. The syringe can be used to advance the fluid down lumen 166 and out distal port 168. The instrument can also have more than one fluid lumen and more than one distal port. Distal ports can be disposed on the distal end of the instrument and/or disposed along the sides, top, and bottom of the instrument, or any combination thereof.

In some methods of use a lubricating agent is applied to an outer surface or surfaces of the instrument before it is advanced under the flap. The lubricating agent decreases the resistance to the instrument as it is advanced through the cornea. A lubricating agent can be applied to an outer surface of an instrument regardless of whether it has a lumen therein.

Figure 13:
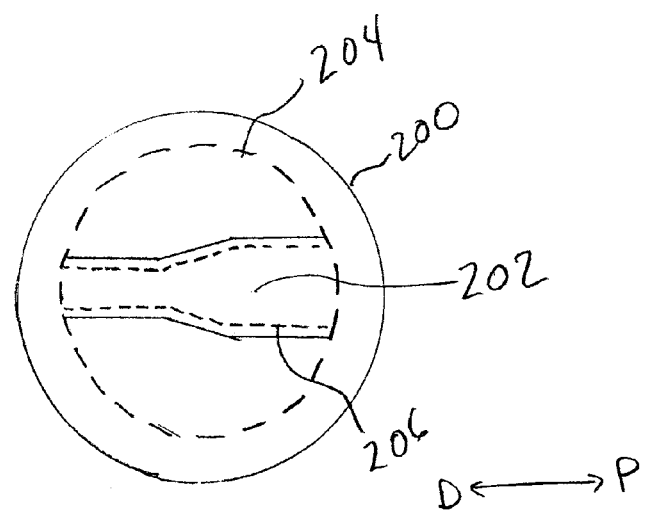
FIG. 13 illustrates an exemplary corneal channel.

In some methods of creating a corneal channel, after the corneal tissue is disrupted (generally the initial step in the process), it is beneficial to create a peripheral side cut that does not define a generally circular shape (when viewed from above). Alternatively stated, it may be beneficial to create a flap wherein the side cut is substantially less than 360 degrees. In LASIK procedures, to the contrary, after the laser disrupts the deeper corneal tissue, the laser makes a peripheral generally circular side cut close to the surface of the cornea that extends almost 360 degrees (with a hinge the side cut is slightly less than 360 degrees, for example, about 300 degrees). FIG. 13 illustrates a first step of a procedure in which a non-circular flap 202 is created in cornea 200. This can be performed with a laser, such as a femtosecond laser. Rather than creating a generally circular side cut 204 extending about 360 degrees (shown in phantom), flap 202 is created that has a generally non-circular side cut. The side cut subtends an angle less than the generally 300-360 degree angle created when creating a traditional flap. The angle can be less than about 270 degrees, less than about 180 degrees, less than about 90 degrees, less than about 60 degrees, less than about 45 degrees, less than about 30 degrees, or less than about 15 degrees. As shown in FIG. 13, the flap has an entry region where an entry side cut has been created (to the right on the page) and an exit region where an exit side cut has been created (to the left on the page). The entry region's side cut subtends an angle of roughly 45 degrees, while the exit region's side cut subtends an angle of roughly 30 degrees. These angles are merely exemplary and are not limiting. When more than one unique side cut is made (e.g., when an entry region and an exit region are created), each cut can have any of the exemplary angles provided above. For example, in FIG. 13, the entry region's side cut and the exit region's side cut are each less than about 60 degrees, and combined are less than about 90 degrees. While only two regions are shown (an entry region and exit region), there may also be more than two created in the cornea.

After the corneal tissue has been disrupted and the side cuts are created, the channel instrument is advanced through the side cuts and into the corneal tissue to create the channel. In some embodiments the side cut angle is greater than the angle which the instrument subtends as it passes through the side cut and into the corneal tissue. For example, if an entry side cut of about 45 degrees is made, the channel instrument may only subtend an angle of about 30 degrees as it is advanced through the entry side cut. Alternatively, if an exit side cut subtends about 30 degrees, the instrument may only subtend an angle of about 20 degrees as it exits the exit side cut. These angles are not limiting and are provided by way of example.

In the embodiment shown in FIG. 13, flap 202 is created to have a shape that resembles the shape defined by the outer edges of the channel instrument. Flap 202 can have dimensions slightly greater than the instrument dimensions to allow the instrument to be safely and efficiently advanced through the cornea. An instrument similar to instrument 20 from FIGS. 2A-3B can be advanced in the direction D from one side of the flap to the other to create channel 206. A corneal implant can then be positioned within the channel.

Figure 14:
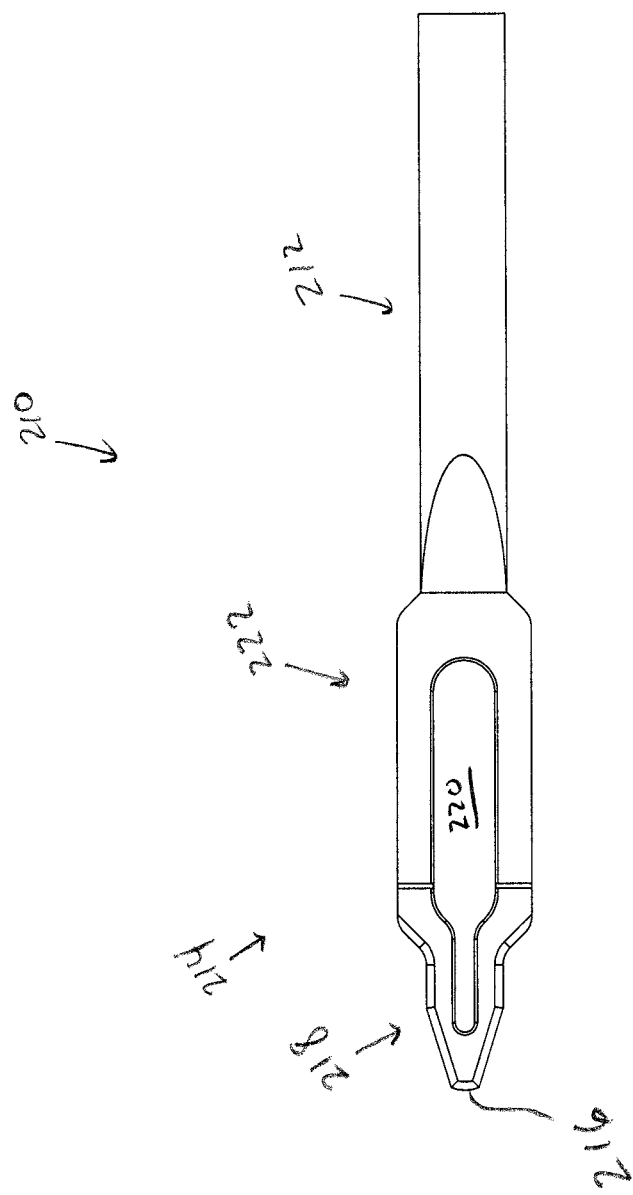
FIG. 14 illustrates an exemplary corneal channel instrument.

FIG. 14 illustrates a top view of an exemplary embodiment of a corneal channel instrument. Instrument 210 includes handle portion 212 and channel portion 214. Channel portion includes distal end 216 and intermediate region 218. The distal end and intermediate region have double-beveled edges to ease the insertion of the instrument through the cornea. An inner surface of channel portion 214 defines opening or window 220, which can alternatively extend only through proximal region 222. The embodiment in FIG. 8 can be used to create a corneal channel as described herein.

In alternative methods of use, the corneal channel instruments described herein can be used to create a channel in the cornea of subjects who have undergone a LASIK procedure. LASIK procedures generally involve creating a flap, folding the flap back to expose the corneal bed, remodeling the exposed corneal tissue, and repositioning the flap back down over corneal tissue. Creating the flap can be performed using a mechanical microkeratome (e.g., a bladed instrument) to disrupt the corneal tissue. Alternatively, the flap can also be created using a laser, such as a femtosecond laser (e.g., as is described above in step 12 of FIG. 1), followed by gentle breaking of the tags. In the latter case, the tags are generally broken using an instrument such as a spatula, etc. Alternatively, any of the channel maker instruments described herein can be used to break the tags during a LASIK procedure. After the flap is folded back, the corneal tissue is remodeled, and the flap is repositioned. The cornea undergoes a healing response after the flap is repositioned. The epithelial layer heals around the periphery of the flap after the flap is repositioned. Additionally, there is a certain amount of biological material at the interface between the corneal bed and the posterior surface of the flap that provides some adhesion. The channel instrument can be advanced through this material in the cornea to form a channel in the cornea, examples of which are set forth above. In some embodiments a corneal implant, such as a corneal inlay, is then positioned within the channel, exemplary embodiments of which are described herein.

The embodiments shown and described herein are merely exemplary. A channel instrument, or its method of use, need not comprise all of the characteristics shown and described in the embodiments herein. Additionally, a corneal channel instrument or its method of use can include characteristics not shown and described in the embodiments herein.

What is claimed is:

1. A method of creating a channel in a patient's cornea, comprising:
   disrupting corneal tissue to create a first disrupted region of the cornea defined by a plurality of corneal tags; and
   creating a corneal channel across a pupil within the first disrupted region of the cornea by breaking a first portion of the plurality of corneal tags and without breaking a second portion of the plurality of corneal tags, wherein the first region is larger than the corneal channel in a top view of the cornea along an optical axis of the cornea, and wherein the method does not comprise lifting corneal tissue.

2. The method of claim 1 wherein creating the corneal channel comprises advancing a channel instrument into the first region to break the first portion of the plurality of corneal tags.

3. The method of claim 2 wherein the advancing step comprises advancing the channel instrument from a first side of the first disrupted region to a second side of the first disrupted region to create a corneal channel that extends from the first side to the second side of the first disrupted region.

4. The method of claim 2 wherein the advancing step comprises advancing the channel instrument along a substantially linear path from a first side of the first disrupted region to a second side of the first disrupted region.

5. The method of claim 1 further comprising creating a first side cut and a second side cut at a periphery of the first disrupted region, wherein the first and second side cuts each subtend an angle less than about 90 degrees.

6. The method of claim 1 wherein creating a corneal channel creates a channel with a first portion with a first width and a second portion with a second width, wherein the first width is different than the second width.

7. The method of claim 1 wherein disrupting corneal tissue comprises disrupting corneal tissue with a femtosecond laser to create a first disrupted region of the cornea defined by a plurality of corneal tags.

8. The method of claim 1 further comprising creating a peripheral side cut that does not have a generally circular shape.

9. The method of claim 1, further comprising positioning a corneal implant within the corneal channel.

10. The method of claim 9 wherein positioning the corneal implant comprises positioning the corneal implant substantially within the boundaries of the pupil.

11. The method of claim 1, further comprising advancing a corneal implant through the corneal channel within a delivery tool, and implanting the corneal implant within the corneal channel.

12. The method of claim 11 wherein creating the corneal channel comprises creating a corneal channel extending from a first side of the first disrupted region to a second side of the first disrupted region, and wherein advancing the corneal implant comprises advancing the corneal implant through the corneal channel within the delivery tool from the first side of the first disrupted region.

13. The method of claim 12 wherein implanting the corneal implant comprises advancing a removal tool into the corneal channel from the second side of the first disrupted region and removing the implant from the delivery tool with the removal tool.

14. The method of claim 1 wherein creating the corneal channel comprises advancing a channel instrument from a first side of the first disrupted region through corneal tissue without advancing the channel instrument out of a second side of the first disrupted region.

15. A method of creating a channel in a patient's cornea, comprising:

disrupting corneal tissue to create a first disrupted region of the cornea defined by a plurality of corneal tags; and creating a corneal channel across a pupil within the first disrupted region of the cornea by advancing a channel instrument into the first disrupted region to break a first portion of the plurality of corneal tags and without breaking a second portion of the corneal tags, wherein the first region is larger than the corneal channel in a top view of the cornea along an optical axis of the cornea, and wherein the method does not comprise lifting corneal tissue.

16. The method of claim 15 wherein the advancing step comprises advancing the channel instrument from a first side of the first disrupted region to a second side of the first disrupted region to create the corneal channel that extends from the first side to the second side of the first disrupted region.

17. The method of claim 15 wherein the advancing step comprises advancing the channel instrument along a substantially linear path from a first side of the first disrupted region to a second side of the first disrupted region.

18. The method of claim 15 wherein creating a corneal channel creates a channel with a first portion with a first width and a second portion with a second width, wherein the first width is different than the second width.

19. The method of claim 15 further comprising positioning a corneal implant within the corneal channel.

20. The method of claim 19 wherein positioning the corneal implant comprises positioning the corneal implant substantially within the boundaries of the pupil.

21. The method of claim 15 further comprising advancing a corneal implant through the corneal channel within a delivery tool, and implanting the corneal implant within the corneal channel.

22. The method of claim 21 wherein creating the corneal channel comprises creating a corneal channel extending from a first side of the first disrupted region to a second side of the first disrupted region, and wherein advancing the corneal implant comprises advancing the corneal implant through the corneal channel within the delivery tool from the first side of the first disrupted region.

23. The method of claim 22 wherein implanting the corneal implant comprises advancing a removal tool into the corneal channel from the second side of the first disrupted region and removing the implant from the delivery tool with the removal tool.

* * * * *